United States Patent
Epel et al.

(10) Patent No.: US 12,298,375 B2
(45) Date of Patent: May 13, 2025

(54) PULSE SEQUENCE FOR RESONANCE-BASED TISSUE ANALYSIS

(71) Applicant: O2M Technologies, LLC, Chicago, IL (US)

(72) Inventors: Boris Meerovich Epel, Chicago, IL (US); Mrignayani Kotecha, Chicago, IL (US)

(73) Assignee: O2M Technologies, LLC, Chicago, IL (US)

(*) Notice: Subject to any disclaimer, the term of this patent is extended or adjusted under 35 U.S.C. 154(b) by 0 days.

(21) Appl. No.: 18/793,584

(22) Filed: Aug. 2, 2024

(65) Prior Publication Data
US 2025/0044392 A1 Feb. 6, 2025

Related U.S. Application Data (60) Provisional application No. 63/517,471, filed on Aug. 3, 2023.

(51) Int. Cl.
G01R 33/60 (2006.01)
A61B 5/055 (2006.01)

(52) U.S. Cl.
CPC .............. *G01R 33/60* (2013.01); *A61B 5/055* (2013.01)

(58) Field of Classification Search
CPC ................................ G01R 33/60; A61B 5/055
See application file for complete search history.

(56) References Cited

U.S. PATENT DOCUMENTS

| | | | | |
|---|---|---|---|---|
| 5,175,499 A | * | 12/1992 | Davies | G01R 33/281 324/308 |
| 9,702,953 B1 | * | 7/2017 | Xiao | G01R 33/56 |
| 10,473,601 B1 | * | 11/2019 | Vashaee | G01N 24/081 |
| 2011/0204892 A1 | * | 8/2011 | Li | G01V 3/32 324/309 |
| 2011/0313279 A1 | * | 12/2011 | Subramanian | G01R 33/485 600/420 |
| 2013/0082708 A1 | * | 4/2013 | Yokosawa | A61B 5/055 324/309 |

(Continued)

OTHER PUBLICATIONS

B. Epel, et al., Absolute Oxygen R1e Imaging In Vivo with Pulse Electron Paramagnetic Resonance, Magnetic Resonance in Medicine 72:362-368 (Year: 2014).*

(Continued)

*Primary Examiner* — Steven L Yeninas
(74) *Attorney, Agent, or Firm* — Lemaire Patent Law Firm, P.L.L.C.

(57) ABSTRACT

A method for relaxation time determination includes delivering a series of radio frequency (RF) pulses in a sequence to a specimen having a magnetic resonance spin system. The pulses are separated by equal time intervals and the sequence has a duration comparable or greater than a spin-lattice relaxation time for the spin system. The method includes receiving a response after each RF pulse in the series. The response includes a free induction decay and spin echoes. The method includes generating a series of single point imaging (SPI) images from each response. Each SPI image of the series corresponds to an RF pulse in the series. The method includes converting SPI images to a spin-spin relaxation map and a spin-lattice relaxation map.

11 Claims, 7 Drawing Sheets

(56) References Cited

U.S. PATENT DOCUMENTS

| | | | |
|---|---|---|---|
| 2014/0103928 A1* | 4/2014 | Grodzki | G01R 33/4828 324/309 |
| 2018/0231626 A1* | 8/2018 | Gulani | G01R 33/4826 |
| 2021/0208227 A1* | 7/2021 | Hardy | G01R 33/56545 |

OTHER PUBLICATIONS

S. Subramanian, et al., Single-Point (Constant-Time) Imaging in Radiofrequency Fourier Transform Electron Paramagnetic Resonance, Magnetic Resonance in Medicine 48:370-379 (Year: 2002).*

B. Epel, et al., How In Vivo EPR Measures and Images Oxygen; Oxygen Transport to Tissue XXXVI, Advances in Experimental Medicine and Biology 812, DOI 10.1007/978-1-4939-0620-8_15, (Year: 2014).*

T.D. Gluth, et al., Biocompatible Monophosphonated Trityl Spin Probe, HOPE71, for In Vivo Measurement of pO2, pH, and [Pi] by Electron Paramagnetic Resonance Spectroscopy; Anal. Chem. 2023, 95, 946-954 (Year: 2023).*

O. Heid, et al., Rapid Single Point (RASP) Imaging (Year: 1995).*

Boris, B., "How in vivo EPR measures and images oxygen", Adv Exp Med Biol. 2014;812:113-9, (2014), 8 pgs.

Chou, CC, "Accelerated electron paramagnetic resonance imaging using partial Fourier compressed sensing reconstruction", Magn Reson Imaging. Apr. 2017 ; 37: 90-99, (Apr. 2017), 19 pgs.

Epel, B., "Absolute oxygen R1e imaging in vivo with pulse electron paramagnetic resonance.", Magn Reson Med. 2014;72(2):362-8., (2014), 7 pgs.

Epel, Boris, "Comparison of pulse sequences for R1-based electron paramagnetic resonance oxygen imaging", J Magn Reson. May 2015 ; 254: 56-61, (May 2015), 18 pgs.

Gluth, Teresa, "Biocompatible Monophosphonated Trityl Spin Probe, HOPE71, for In Vivo Measurement of pO(2), pH, and [P(i)] by Electron Paramagnetic Resonance Spectroscopy", Anal Chem. Jan. 17, 2023; 95(2): 946-954, (Jan. 17, 2023), 18 pgs.

Matsumoto, Ken-Ichiro, "Electron Paramagnetic Resonance Imaging of Tumor Hypoxia: Enhanced Spatial and Temporal Resolution for In Vivo pO2 Determination", Magnetic Resonance in Medicine 55:1157-1163 (2006), (Apr. 4, 2006), 7 pgs.

Subramanian, Sankaran, "Echo-based Single Point Imaging (ESPI): A Novel Pulsed EPR Imaging Modality for High Spatial Resolution and Quantitative Oximetry", J Magn Reson. May 2012 , 218, 105-114, (May 2012), 28 pgs.

Di Giuseppe, S., "Pulsed EPR imaging: image reconstruction using selective acquisition sequences", Physics in Medicine and Biology 44.6, (1999), N137.

Kishimoto, Shun, "Pulsed electron paramagnetic resonance imaging: applications in the studies of tumor physiology", Antioxidants and redox signaling 28.15, (2018), 1378-1393.

Subramanian, Sankaran, "Dancing with the electrons: time-domain and CW in vivo EPR imaging", Magnetic resonance insights 2, (2008), MRI-S1131.

* cited by examiner

PULSE SEQUENCE FOR RESONANCE-BASED TISSUE ANALYSIS

CLAIM OF PRIORITY

This patent application claims the benefit of priority of U.S. Provisional Patent Application No. 63/517,471, filed on Aug. 3, 2023, which is hereby incorporated by reference herein in its entirety.

TECHNICAL FIELD

This document pertains generally, but not by way of limitation, to electron paramagnetic resonance spectroscopy and electron paramagnetic resonance imaging.

BACKGROUND

Electron paramagnetic resonance (EPR), also known as electron spin resonance (ESR), is a magnetic resonance method that observes the unpaired electrons (also referred here as electron spins) under a constant magnetic field. Pulse EPR is a subset of EPR methods that utilizes radiofrequency pulses of alternating magnetic field ($B_1$, also known as the transverse magnetic field) to manipulate electron spins' magnetization. Pulse EPR imaging (pEPRI) utilizes magnetic field gradients to generate three-dimensional maps of parameters of interest.

Conventional pulse EPR sequences seek to determine a single parameter of interest such as relaxation times $T_1$ or $T_2$. EPR signals after multiple sequences of radio frequency (RF) pulses with different delays are recorded. The sequence alterations are configured to impose a parameter-dependent (such as a $T_1$) change in the signals. These sequences are parameter-specific and thus more precise but the overall experiment is lengthy because of multiple acquisitions separated by time comparable to multiples of $T_1$'s, long enough to allow the equilibration of the spin system.

Spatial EPR imaging requires the acquisition of a large number of EPR signals in the presence of different magnetic field gradients. Relaxation times imaging further increases the number of acquisitions resulting in long image duration.

SUMMARY

This document describes an imaging method based on single point imaging (SPI) methodology extended to imaging of relaxation times $T_1$ and $T_2$ while maintaining image quality and resolution and increasing the number of measurements at different gradients as compared to conventional SPI. This method is free from the technical limitations of the saturation by repetition time (SRT) method.

The disclosed pulse sequence includes a series of radio frequency pulses separated by equal time intervals with the overall duration of the sequence longer than relaxation time $T_1$ and equilibration time between RF pulses and spin system. The equilibration here is understood as an absence of further changes in detected signals observed after the application of additional pulses in the sequence. Under these conditions, the amplitudes of free induction decay after each pulse, and spin echoes become dependent on $T_1$, $T_2$ and time from the beginning of the sequence. The sequence can be repeated multiple times for signal averaging after the delay $T_{REP}$ much longer than $T_1$, which can be chosen from application-specific considerations, such as desired duty cycle or overall power deposition. The multitude of SPI images produced from the detected signals (including free induction decays and spin echoes) can be converted into a $T_1$ map. In addition to $T_1$, other parameters affecting EPR signals, such as $T_2$ and $B_1$ can be obtained from the same measurement.

The method is based on acquiring $T_1$ and $T_2$-dependent signal evolution within a single sequence of RF pulses rather than using a $T_1$-equilibrated average over multiple sequences.

In one example, a sequence of identical 90-degree RF pulses separated by identical time intervals, each of them a fraction of $T_1$, can be used. In another example, a sequence of pulses with linearly increasing amplitudes (from zero to the highest amplitude corresponding to a 90-degree pulse) can be used. Each of these non-limiting examples can stand on its own or can be combined in various permutations or combinations with one or more of the other examples.

This document also describes a method of phase cycling for the above sequences that allows the separation of free induction decay, spin echo, and stimulated echo signals for proper SPI image formation. For that, the data from multiple pulse sequences in which the phases of radio frequency pulses are altered (according to the disclosed algorithm) are acquired. Then, multiple linear combinations of the acquired signals are formed representing free induction decay, spin echo or stimulated echo signals. The coefficients for the linear combinations are selected to leave one of the types of EPR signals and cancel another.

This document also describes a method for obtaining parameters such as $T_1$ or $T_2$ from the signal evolution produced by the above sequences. Parameters are extracted by matching the time evolution of the SPI images to the numerical simulations employing the Bloch equation or to a pre-measured library of signals.

Pulse electron paramagnetic resonance (EPR), sometimes referred to as electron spin resonance (ESR), is a magnetic resonance method where electron spins, subjected to a constant magnetic field, are excited using radiofrequency pulses. Pulse EPR can be used to obtain many electron spin parameters including spin-lattice relaxation time ($T_1$) and spin-spin relaxation time ($T_2$). For some spin probes, oxygen partial pressure (p$O_2$) is linearly proportional to relaxation rates. These probes can be used for EPR oximetry. Most precise pO2 measurements can be obtained using spin-lattice relaxation time. Pulse EPR imaging (pEPRI) provides a method to generate three-dimensional maps of EPR signals. Single Point Imaging (SPI) is one of the best methods to produce high-resolution EPR images. However, some SPI methods for imaging relaxation times either sacrifice image resolution or increase the number of measurements with different magnetic field gradients for each image. This reduces image quality and increases image duration. Imaging $T_1$ using SPI is especially challenging.

This document discloses an imaging method based on SPI for imaging $T_1$ and $T_2$ without reducing imaging resolution and without an increase in the number of measurements at different gradients.

Also disclosed is a method, which is suitable for electron spin echo (ESE) imaging. This method is capable of $T_2$ imaging. A variant of this method for $T_1$ imaging is called inversion recovery electron spin echo imaging or IRESE. The disclosed method includes applying of a Carr-Purcell-Meiboom-Gill (CPMG) pulse sequence with the overall duration of sequence longer than relaxation time $T_1$ and equilibration time between RF pulses and spin system. Under these conditions, the amplitude of spin echoes becomes dependent on $T_1$ and delay from the first pulse in the sequence. ESE images produced from each echo can be converted into $T_1$ maps. In addition to $T_1$, other parameters such as $T_2$, and $B_1$ can be obtained. Parameters are extracted by matching the time evolution of the acquired signals to the numerical simulations employing the Bloch equation or to a pre-measured library of signals.

This overview is intended to provide an overview of the subject matter of the present patent application. It is not intended to provide an exclusive or exhaustive explanation of the invention. A detailed description is included to provide further information.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Instrumentation

Figure 1:
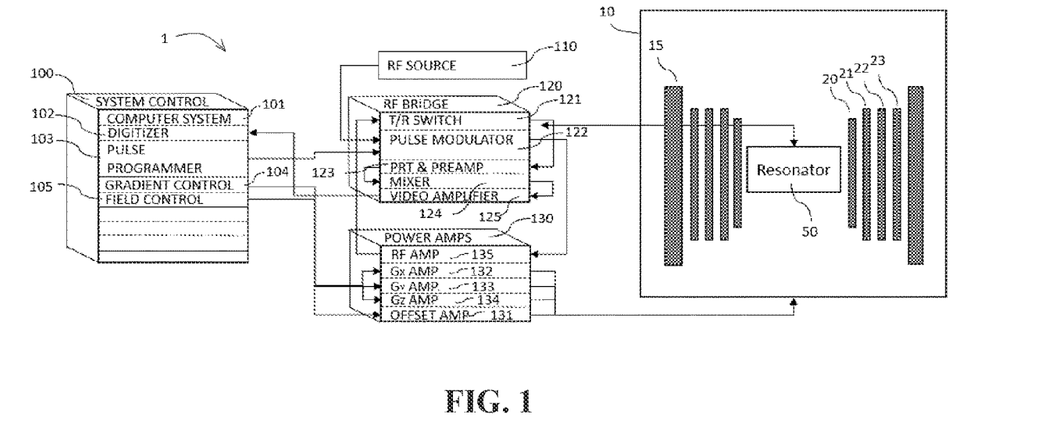
FIG. 1 illustrates a system, according to an example of the present subject matter.

FIG. 1 includes a system diagram illustrating an electron paramagnetic resonance imaging (EPRI) system 1. EPRI system 1 includes an EPR magnet assembly 10, system control 100, RF source 110, RF bridge 120, and power amplifiers 130. In addition, the example here can include mechanical stage actuators and mass flow gas controllers. A base platform can serve as a support for resonators and mechanical stages. The units shown here can be housed together in one unit or can be provided in various combinations.

EPR magnet assembly 10 includes a permanent magnet 15, field offset coils 20, three orthogonal gradients coils Gx 21, Gy 22, and Gz 23, and loop-gap resonator 50. The magnet coils are connected to power amplifier unit 130 including offset field amplifier 131, and gradient amplifiers 132, 133, and 134.

The RF bridge 120 receives the basic frequency from RF source 110. The pulse modulator 122 of the bridge uses a combination of RF switches and phase shifters activated by the pulse sequence produced by pulse programmer 103 to generate the pulse sequence. The pulse sequence is fed to power amplifier 130 and then fed into RF bridge 120, which directs excitation power to the reflection type resonator 50 and then routes the detected signals to the preamplifier 123. Preamplifier 123 can include protection circuitry to prevent damage from high power. The detected signals are downconverted using mixer 124 and LO signal from source 110, amplified by video amplifier 125, and then digitized by digitizer 102.

Control 100 includes a computer system 101 with hardware controllers including signal digitizer 102, pulse programmer 103, gradient 104 and field 105 controllers. Computer system 101 can be configured to execute, among other things, image acquisition software, image reconstruction software, software for image processing, and visualization software.

Figure 2:
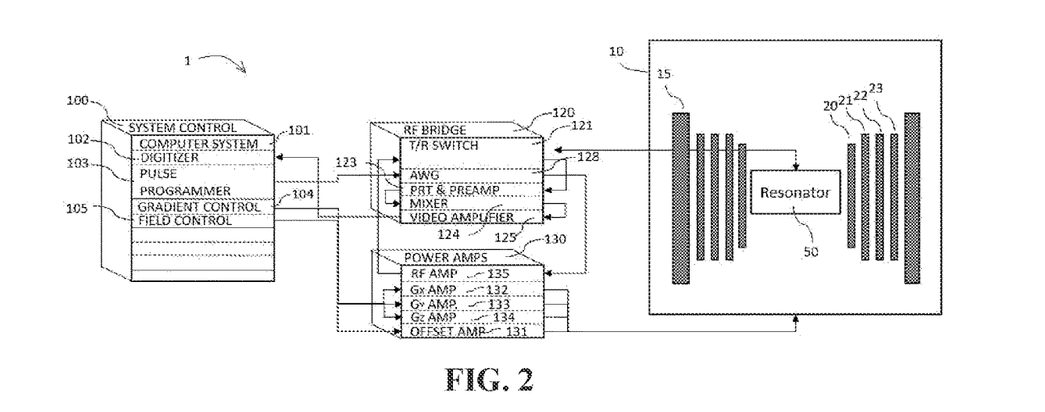
FIG. 2 illustrates a system, according to an example of the present subject matter.

Another example of a system is shown in FIG. 2. The system of FIG. 2 can be configured to provide customization of the pulse sequence. Here a computer-controlled arbitrary waveform generator (AWG) 128 is used to generate pulse sequences. AWG generation is not limited to RF pulses of square shape and four different phases but can generate arbitrary RF pulses with any shape, phase, or amplitude. AWG 128 may provide additional flexibility in imaging and data analysis.

EPR Imaging

Pulse electron paramagnetic resonance (pEPRI) can be used for spatial and parametric imaging of electron spins. The electron spins have relaxation times in the range from hundreds of nanoseconds to a few microseconds. A typical spin probe used for pulse EPR in vivo oxygen imaging is trityl OX071 probe with $T_1$, $T_2$, and $T_2^*$ relaxation times of 8.4 µs, 3.9 µs, and 1.11 µs, respectively (relaxation times are given at 25 mT for 1 mM OX071 dissolved in phosphate buffer saline (PBS) at 0% oxygen and at room temperature). OXO71 $T_1$ and $T_2$ further reduce about 10-fold for 21% oxygen conditions. These very short relaxation times prevent the use of pulse magnetic field gradients for non-microscopic objects.

pEPRI imaging methods utilizing static magnetic field gradients are electron spin echo (ESE) and single-point imaging (SPI). See Epel B et al. Absolute oxygen R1e imaging in vivo with pulse electron paramagnetic resonance. Magn Reson Med. 2014; 72(2):362-8. doi: 10.1002/mrm.24926; Subramanian S et al. Single-point (constant-time) imaging in radiofrequency Fourier transform electron paramagnetic resonance. Magn Reson Med. 2002; 48(2): 370-9. doi: 10.1002/mrm.10199. The applications of these methods for obtaining $T_1$ and $T_2$ maps are demonstrated along with numerous biomedical and material science applications, such as obtaining tissue oxygen maps that rely on the linear relationship between $R_1$ (=$1/T_1$) and $R_2$ (=$1/T_2$) relaxation rate and tissue partial oxygen pressure maps using trityls OX063 or OX071 as a source of electron spins. See Epel B et al. Absolute oxygen R1e imaging in vivo with pulse electron paramagnetic resonance. Magn Reson Med. 2014; 72(2):362-8. doi: 10.1002/mrm.24926; Subramanian S et al. Single-point (constant-time) imaging in radio frequency Fourier transform electron paramagnetic resonance. Magn Reson Med. 2002; 48(2):370-9. doi: 10.1002/mrm.10199; Epel B, Redler G, Halpern H J. How in vivo EPR measures and images oxygen. Adv Exp Med Biol. 2014; 812:113-9. doi: 10.1007/978-1-4939-0620-8_15.

Another application includes obtaining tissue pH maps using Monophosphonated trityl. See Gluth T D et al., Biocompatible Monophosphonated Trityl Spin Probe, HOPE71, for In Vivo Measurement of pO(2), pH, and [P(i)] by Electron Paramagnetic Resonance Spectroscopy. Anal Chem. 2023; 95(2):946-54. doi: 10.1021/acs.analchem.2c03476).

The EPRF method described here can be used to obtain tissue $pO_2$, pH or redox potential maps, that can be used for a wide variety of applications such as cancer, tissue engineering regenerative medicine, neurodegenerative diseases, kidney and liver diseases, trauma, wound healing, stroke and ischemia, etc.

Imaging Basic Concepts

A spatial image, as referred to herein, includes a three-dimensional image of spin-probe concentration in a discrete form and can be represented by a three-dimensional matrix. A voxel is a single element of this matrix. The value of each image voxel represents the number of spin probe molecules located within a voxel. Three-dimensional Fourier transformation (3DFT) of the spatial image matrix R produces a complex three-dimensional matrix K in a space designated as k-space as referred to herein. The signals S(t) acquired by pEPR can be mapped to k-space voxels. The inverse 3DFT of the K generates a spatial image.

Multiple strategies of k-space signal acquisition can be described. The coordinate of the k-space point is given by $\vec{k}=2\pi\gamma\vec{G}t$, where $\vec{G}=[Gx, Gy, Gz]$, is a static gradient vector, t is time after the beginning of encoding, and $\gamma$ is the gyromagnetic ratio of the electron. For linear gradient encoding, each element of the EPR signal at times t can be mapped to a unique k-space point along a line defined by the gradient vector. Alternatively, a static gradient $\vec{G}$ can be changed to acquire the same k-space point at the fixed time t. The encoding in which multiple elements of EPR signal S(t) are mapped, is called frequency encoding while encoding in which a single time point of EPR signal $t=t_p$ is used is called phase encoding. A combination of these encoding methods can be used for MRI but in pEPRI of large objects, a purely phase or frequency encoding is used due to the hardware limitations.

In one example, a complete k-space of data is acquired by varying the gradient $\vec{G}$ vector while the acquisition point is fixed at $t=t_p$ after a single 90-degree pulse. This method can be described as a single point imaging, SPI. 3D Fourier Transform (FT) of the k-space matrix can be used to reconstruct the spatial image. To acquire relaxation time $T_2^*$ map, multiple points $t_{p1}$ to $t_{p2}$ of the EPR signal can be taken and multiple images can be reconstructed. Because these images have different spatial extents, a procedure to equalize their resolution can be used involving image interpolation. After that, images can be stacked into a 4D matrix in which the fourth dimension can be a time evolution of the EPR signal along time axis $t_{p1}$ to $t_{p2}$ and time evolution can be fit to exponential decay to extract relaxation time $T_2^*$.

Image interpolation can result in severe artifacts in $T_2^*$ maps. An example method can be utilized to resolve this issue. In this method, for each $t_p$, a separate gradient grid calculated to deliver identical k-space can be acquired. This solves the interpolation problem but demands a large number of measurements at different gradients to be performed. As a result, a combination method in which only a few grids are acquired, and other images are produced using interpolation can be used.

In one example, a method utilizes SPI in combination with a pulse sequence including 90-degree and 180-degree pulses separated by the delay tau. Here, the sequence can be used to generate one free induction decay and one spin echo. In this method, three points can be used for image reconstruction. The point of free induction decay after the first pulse at tp and two points at times $-t_p$ and $t_p$ on rising and falling portions of the spin echo centered at the delay 2*tau after the first pulse. The intensity of the spin-echo signal is $T_2$ dependent and thus this imaging method can map $T_2$.

In one example, imaging is performed until the complete k-space matrix is filled with data. Alternatively, the k-space matrix can be filled partially, and missing data can be filled using a predictive algorithm.

See Epel B et al. Absolute oxygen $R_{1e}$ imaging in vivo with pulse electron paramagnetic resonance. Magn Reson Med. 2014; 72(2):362-8. doi: 10.1002/mrm.24926 and U.S. Pat. No. 9,392,957 for imaging spin-lattice relaxation time $T_1$ vs spin-spin relaxation time $T_2$ for in vivo and in vitro oximetry. Oxygen concentration equally affects $T_1$ and $T_2$ however $T_2$ has approximately 4-8 times higher contribution from spin probe concentration which biases oxygen measurement. Thus, for oxygen imaging $T_2^*$ relaxation maps and $T_2$ relaxation maps that can be derived from them can not deliver as precise oxygen determination as $T_1$ maps.

In one example, two methods can determine $T_1$ and are compatible with SPI. One method can use repetition time saturation in which multiple SPI images with different repetition times between pulses, $T_{REP}$, can be acquired. $T_1$ is then extracted from the fitting of each spatial voxel $T_{REP}$ dependence to $S(T_{REP})=A\exp(-T_{REP}/T_1)$ function. While this method allows acquiring $T_1$-dependent images at single $t_p$ and avoids imaging artifacts, it also is subject to severe hardware limitations as determination of small $T_1$ requires small $T_{REP}$. The hardware limitations on the maximum duty cycle and maximum power deposition, rendered this method incapable of performing well under experimental conditions. A second method can use an additional 180-degree inversion pulse separated by the delay T before a 90-degree pulse of SPI. This pulse imposes a $T_1$-dependence on the detected signal $$S(T) = A\left(1 - 2*\exp\left(-\frac{T}{T_1}\right)\right)$$

and allows $T_1$ determination. While applicable to a wide range of $T_1$, this method is disadvantageous since it imposes long $T_{REP}$ that slows down the acquisition and does not allow for efficient averaging. In addition, the power deposition of the 2-pulse sequence is quite large.

A nuclear magnetic resonance fingerprinting (MRF) sequence can generate unique signal evolutions using a combination of different acquisition parameters. MRF simultaneously generates quantitative maps by analyzing acquired spatially and temporally incoherent signals in light of a pre-calculated dictionary. Instead of working to produce a constant signal, MRF embraces signal dynamics by varying acquisition parameters. For example, flip angle and repetition time can be varied to generate unique signal evolutions for different tissue types.

MRF is described in Ma D, Gulani V, Seiberlich N, Liu K, Sunshine J, Duerk J, and Griswold M. Magnet Resonance Fingerprinting, Nature, 495:187-192 (2013). MRF is also described in U.S. patent application Ser. No. 13/051,144 filed Mar. 18, 2011 by Griswold et al., and in U.S. patent application Ser. No. 13/623,104 filed Sep. 19, 2012 by Griswold et al.

Method

As used herein, a four-dimensional image is formed by simultaneous or sequential acquisition of n spatial images. Spatial images are reconstructed independently and then stacked to form a four-dimensional image. The parameters of acquisition or pulse sequence are selected such that the evolution of image amplitude in the fourth dimension can be used to determine spin-lattice relaxation time $T_1$, spin-spin relaxation time $T_2$, dephasing time $T_2^*$, constant magnetic field $B_0$, radio frequency magnetic field $B_1$, or other parameter of interest. A parametric image, as referred to herein, is a three-dimensional image in which each image voxel represents the value of a parameter associated with a spatial location. A parametric image is formed by per-voxel extracting of parameter value from the fourth dimension of the four-dimensional image.

EPR Fingerprinting (EPRF), as described here, can be used in combination with Single Point Imaging acquisition (SPI) and electron spin echo imaging (ESE). The relaxation times of EPR spin probes used for imaging are on the order of 1 µs to 15 µs allowing unique evolutions of the spin system before it reaches a steady state for a duration of about 10 µs.

For Single Point Imaging Fingerprinting (SPIF), multiple pulses generating multiple signals can be used. The duration, flipping angle, and delays between pulses can be selected to allow spin system evolution and generate $T_1$ and $T_2$-weighted signals. The number and flipping angles of pulses can be selected so that acquired signals after pulses are not steady. The free induction decays as well as spin-echo signals can be acquired.

Figure 3:
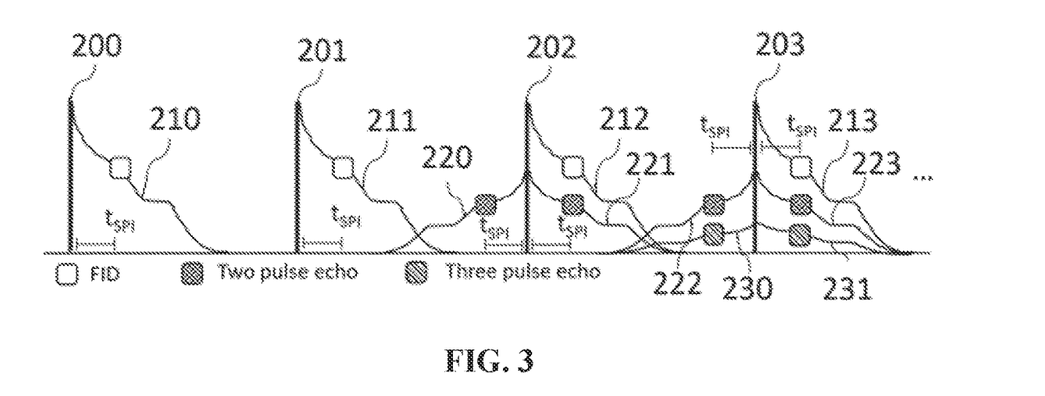
FIG. 3 illustrates signal amplitude as a function of time, according to an example of the present subject matter.

A method, such as depicted in FIG. 3, utilizes a sequence of four or more 90-degree pulses 200, 201, 202, and 203 separated by equal intervals followed by the detection of all generated signals. Each pulse 200, 201, 202, and 203 generates a corresponding free induction decay 210, 211, 212, and 213, respectively, and every two pulses generate a spin echo (e.g. pulses 200 and 201 generate echo with rising slope 220 and falling slope 221), every three pulses generate a stimulated echo (e.g. pulses 200, 201 and 202 generate stimulated echo with rising slope 230 and falling slope 231), each echo in combination with a pulse can generate a new echo, etc. The overall duration of the pulse sequence is comparable to $T_1$ relaxation time, thus forming non-equilibrium acquisition. For signal-to-noise improvement, the sequence of pulses can be repeated with a repetition time considerably longer than $T_1$. In the figure, the detection position at time $t_{SPI}$ is shown with squares. Note that one point from each FID and two points from the rising and falling slopes of the echoes can be used. The duration of the pulses and delays between pulses can be arbitrary, providing the ability to detect signals. The $T_1$, $T_2$, or $T_2^*$ relaxation times and the magnetic field $B_1$ are extracted, for example, by fitting the time evolution of the signals to the Bloch equation. The application of the method to Single Point Imaging and Electron Spin Echo Imaging techniques commonly used in EPR imaging is described.

Figure 4:
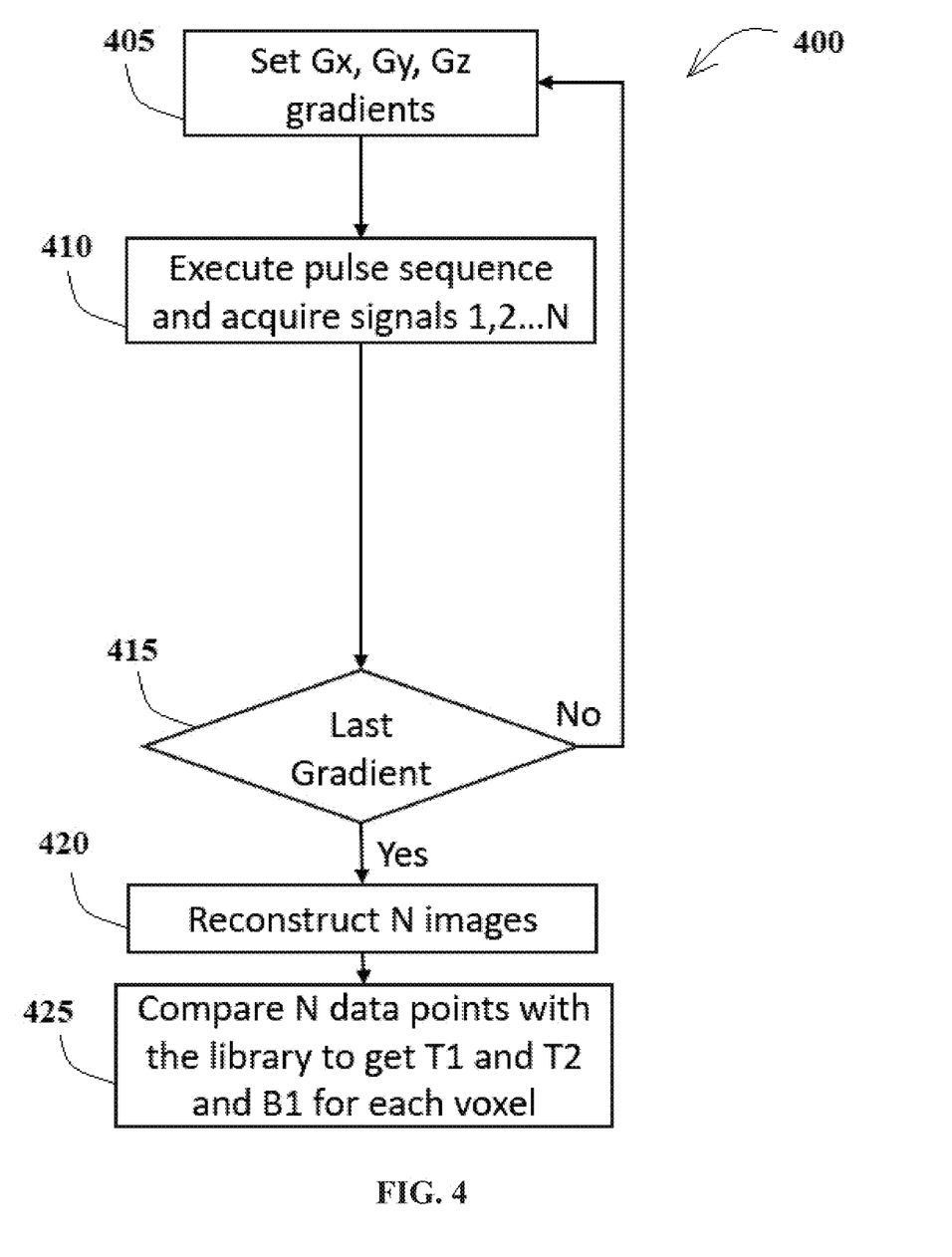
FIG. 4 illustrates a flowchart of a method, according to one example of the present subject matter.
Figure 5:
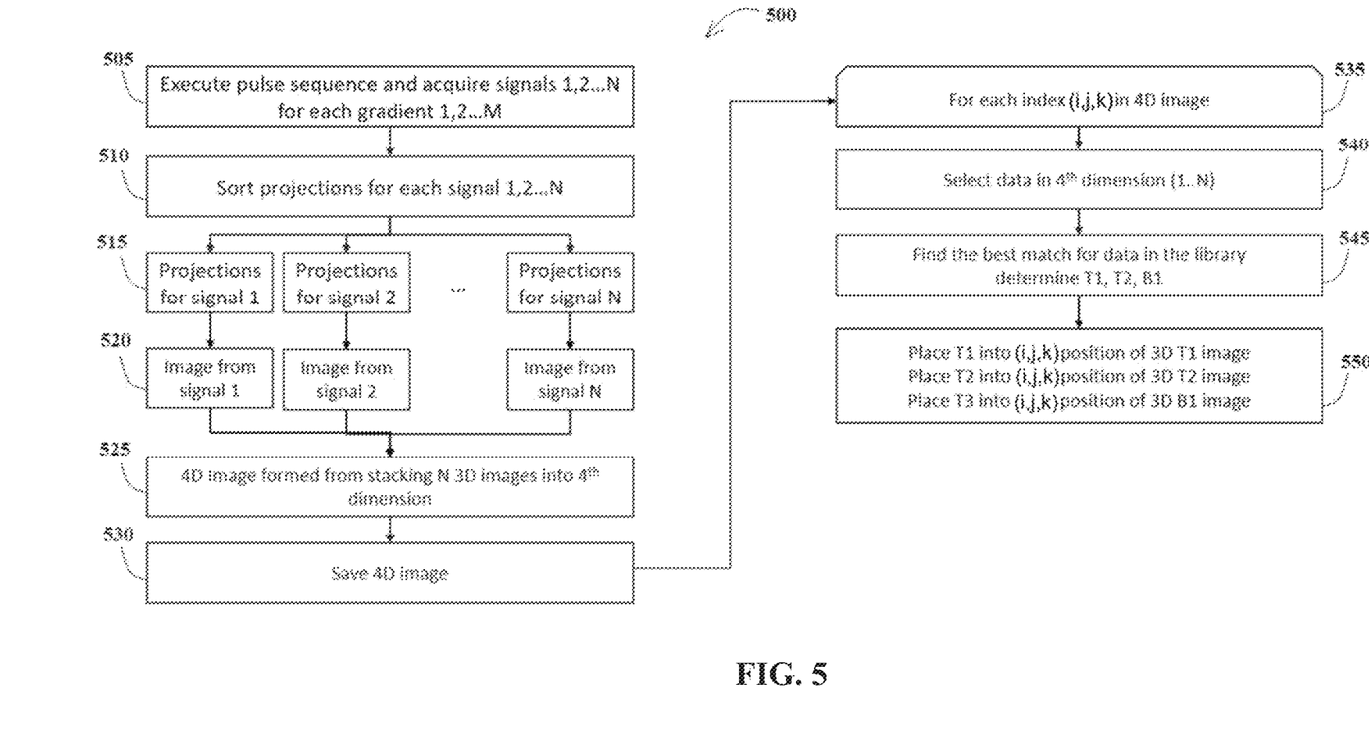
FIG. 5 illustrates a flowchart of a method, according to one example of the present subject matter.

FIGS. 4 and 5 show classic and fingerprinting experiment flow charts, respectively. As illustrated in FIG. 4, all plurality of signals are acquired within a single RF pulse sequence.

FIG. 4 illustrates a flowchart of method 400 for acquiring a plurality of signals using a single RF pulse sequence.

At 405, method 400 includes setting linear magnetic field gradients using coils aligned on the x-axis, y-axis and z-axis, here denoted as gradients Gx, Gy, and Gz. The field gradients are specified based on the image to be generated.

At 410, method 400 include applying an RF pulse sequence and acquiring responses associated with a plurality of signals. The response signals can include a free induction decay, an echo, or other signal.

At 415, method 400 includes an inquiry to determine if additional gradients remain and if not finished, the processing returns to again apply a different gradient, and apply or execute the pulse sequence, and acquire additional signals.

At 420, method 400 includes reconstruction images corresponding to each acquired signal. As shown in the figure, the number of acquired signals aligns with the number of images to be reconstructed.

At 425, method 400 includes comparing the N data points with content in a data store or library to determine relaxation times $T_1$, $T_2$, or field $B_1$ for each voxel in the image.

FIG. 5 illustrates a flowchart of method 500 for acquiring a plurality of signals using a single RF pulse sequence.

At 505, method 500 includes executing a pulse sequence and acquiring signals identified here as 1, 2, . . . N for each gradient identified here as 1, 2, . . . M.

At 510, method 500 includes sorting projections for each signal 1, 2, . . . N.

This is further illustrated at 515, in method 500, wherein for each signal, such as signals 1, 2, . . . N, as shown at 520, an image is received corresponding to each signal 1, 2, . . . N.

As shown at 525, method 500 includes forming 4D image by stacking the signals 1, 2, . . . N to form 3D images to generate a $4^{th}$ dimension.

As shown at 530, method 500 includes storing the 4D image.

As shown at 535, method 500 continues with processing each index (i, j, k) in the 4D image.

At 540, method 500 includes selecting data in the $4^{th}$ dimension—this corresponds to 1, 2, . . . N.

At 545, method 500 includes finding the best match for data in the stored data (library) to determine relaxation times $T_1$, $T_2$, or field $B_1$.

At 550, method 500 includes placing $T_1$ into index (i, j, k) position of 3D $T_1$ image, placing $T_2$ into index (i, j, k) position of 3D $T_2$ image, and placing $T_3$ into index (i, j, k) position of 3D $B_1$ image.

FIG. 5 shows an image processing flow chart. For classic EPR imaging for each gradient set, multiple EPR sequences followed by signal acquisitions are performed. For example, for saturation by repetition time experiment, sequences with different $T_{REP}$ values can be executed. For SPIF, one sequence with multiple acquisition is performed. If the digitizer does not allow multiple acquisitions, one long acquisition can be performed with the separation of signals in postprocessing.

Figure 6:
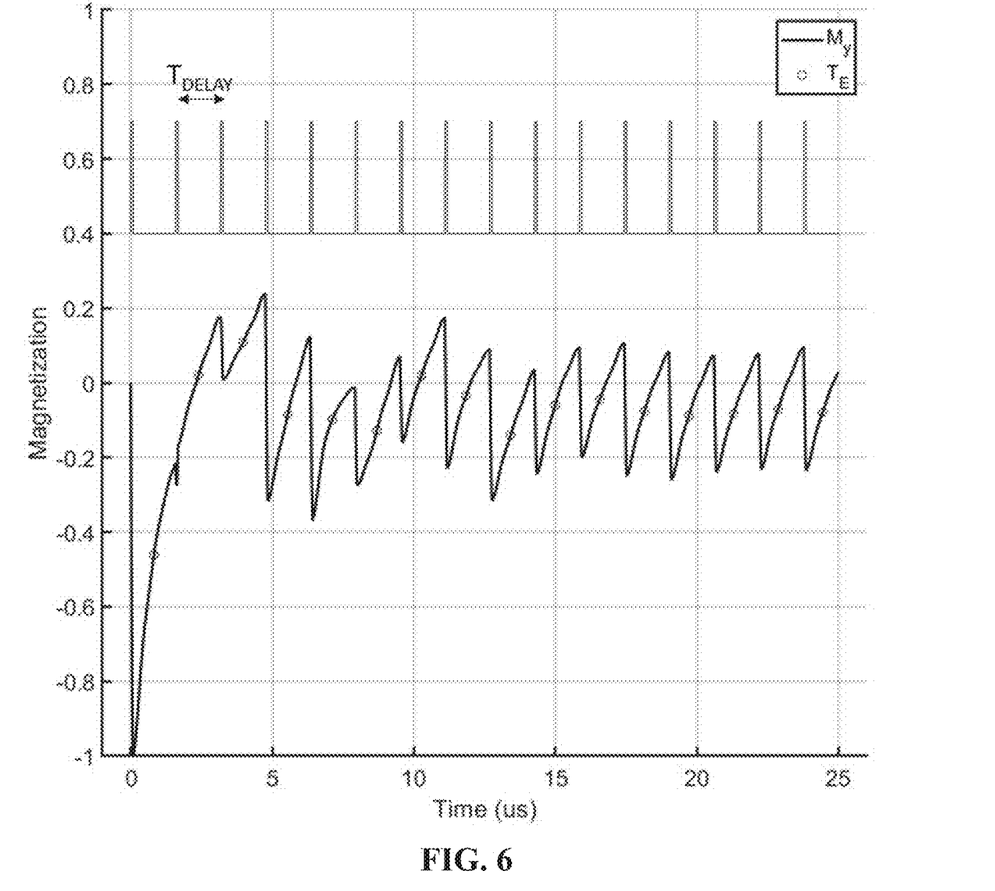
FIG. 6 illustrates magnetization amplitude as a function of time, according to an example of the present subject matter.

In one example, a protocol using SPIF includes multiple 90-degree pulses separated by identical intervals $T_{DELAY}$ followed by the delay $T_{REP}$ considerably longer than the relaxation time of the sample, as shown in FIG. 6. The figure illustrates the simulation of spin-system $M_y$ magnetization (EPR signal) during the SPIF pulse sequence, including 16 RF π/2 pulses separated by $T_{DELAY}$=1.5 µs, $T_{REP}$ is infinite. $T_1$=8 µs, $T_2$=5 µs. SPI signals at $t_{SPI}$=750 ns are marked by empty circles.

Figure 7:
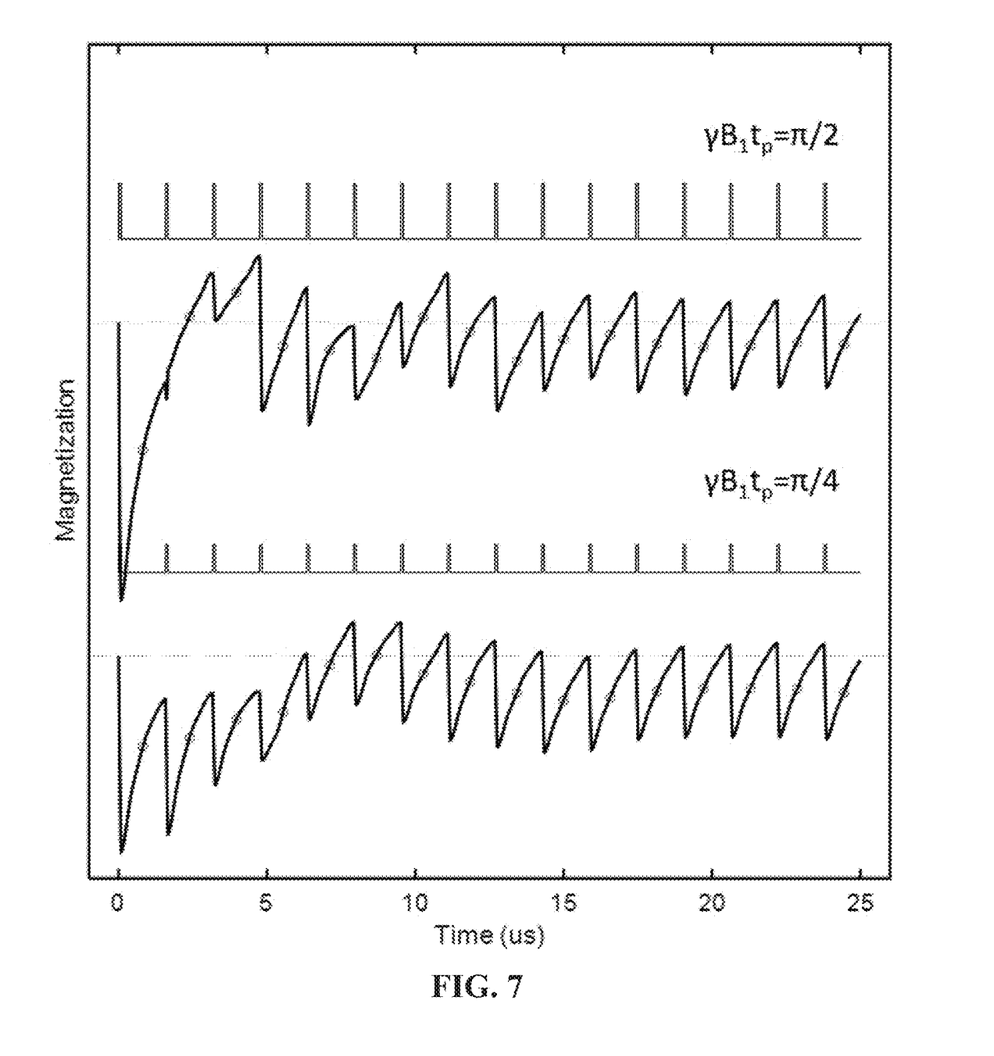
FIG. 7 illustrates magnetization amplitude as a function of time, according to an example of the present subject matter.

In one example, the SPIF sequence can be used for $B_1$ imaging. Here the pulse sequence includes pulses of different turning angles or multiple sequences with pulses having different turning angles. FIG. 7 shows the effect of pulses with different turning angles on the EPR signal. The application of pulses with different turning angles produces distinctly different time traces which allows determining the pulse turning angle.

Figure 8:
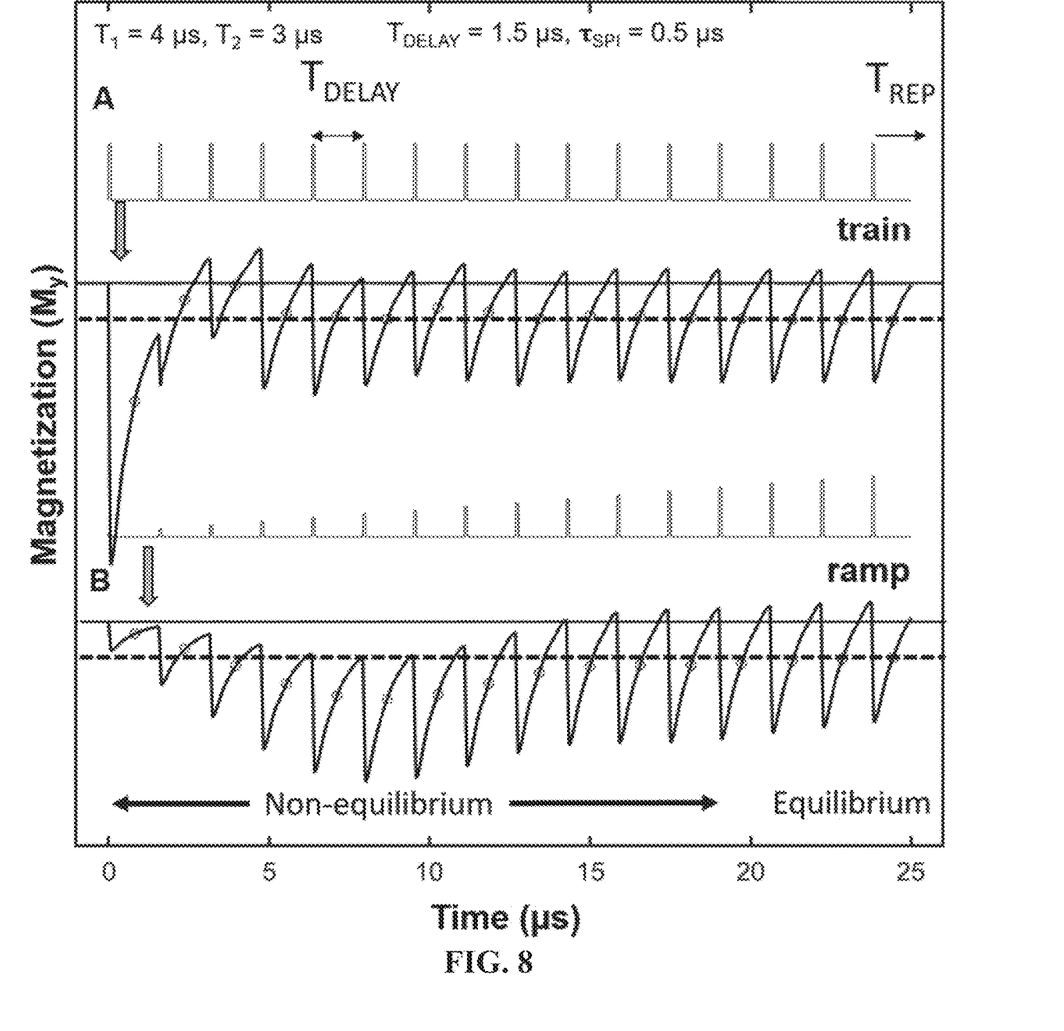
FIG. 8 illustrates magnetization amplitude as a function of time, according to an example of the present subject matter.

In one example, a sequence of pulses with linearly increasing amplitudes from zero to 90-degree pulse amplitude can be used as shown in FIG. 8. This method allows stretching nonequilibrium signal in the time domain, obtaining more points along the time dimension and may lead to increased signal-to-noise ratio of the measurements.

In one example, using SPIF, the true amplitude of the signal corrected for $B_1$ inhomogeneity and effects of $T_1$ and $T_2$ relaxation can be generated.

In one example, the present subject matter includes using trityl OX063 or OX071 to generate quantitative $T_1$, $T_2$ and $B_1$ maps using a low-field pEPRI instrument operating between 1 mT and 42 mT.

Phase Cycling

FIG. 3 illustrates a plurality of EPR signals that can be generated by the SPIF pulse sequence. While most of the signals will result in the generation of correct images, some signals can result in the generation of unwanted images and thus can be removed or separated. In particular, free induction decay (FID) after the second pulse overlaps with the spin echo produced by the first two pulses. Thus, FID signal detected at delay $t_{SPI}$ from the second pulse will overlap with the rising slope of the echo and will have offset $T_{DELAY}-t_{SPI}$ from the time zero of the echo. Image reconstructed from this time point will be composed of overlapped images with different fields of view corresponding to delays $t_{SPI}$ and $T_{DELAY}-t_{SPI}$. To avoid this effect, echo signals can be suppressed. This can be obtained by phase cycling. Each pulse of the sequence can assume four phases 0 deg, 90 deg, 180 deg, 270 deg. In the most general form, multiple sequences that have all possible permutations of four phases are produced and signals are acquired. Then the linear combination of the said signals is obtained with coefficients assuming +1 or −1 values. The coefficient can be selected in a way that allows the canceling of unwanted signals.

Data Fitting, Fingerprinting Approach

The signal points at time duration $t_{SPI}$ after each pulse can be used to form the SPI images. Stacking of SPI images will form a four dimensional image in which the fourth dimension represents the signal evolution after the n-th RF pulse in the sequence. The evolution of the signal along the fourth dimension of the four-dimensional image can be fitted using the Bloch equations. Bloch equations compute the evolution of the magnetization vector of the spin system described by $T_1$, $T_2$, and linewidth during free precession and application of the oscillatory magnetic field $B_1$. In equilibrium, the magnetization vector is found along the z (permanent magnetic field) direction. The signals are detected along the y direction denoted as $M_y$. The fit of the experimental curve to the equation can be obtained both by a multi-parameter fitting routine or by comparison with a pre-calculated library. The pre-calculated library approach is more feasible for rapid image analysis due to the mathematical complexity of the calculations. At the first step, a dictionary of possible signal evolutions can be generated using the Bloch equations or even experimentally by measuring phantoms equilibrated to a known $pO_2$ concentration. The second step involves pattern matching between experimental data and the dictionary and extraction of $T_1$, $T_2$, and $B_1$ from the best-match dictionary entry.

FIG. 6 shows the response of spin system (magnetization projection to y-axis of the revolving coordinate system) to the sequence of equally spaced RF pulses using Bloch equations. The signals at time points used for SPI image reconstruction are marked with open circles. The figure demonstrates that after a few initial RF pulses (about ten for the spin system parameters used in the simulation) the response of the spin system is stabilized, and further RF pulses cause the same response. The SPI images reconstructed from these initial points can be used for determining the relaxation times.

FIG. 7 shows the response of spin system to the sequence of equally spaced RF pulses computed using Bloch equations. The figure illustrates the difference in spin system response to RF pulses of different amplitude. The difference in response allows determination of $B_1$.

FIG. 8 shows the response of spin system to the sequence of equally spaced RF pulses computed using the Bloch equations. The figure illustrates the advantages of ramping the intensity of RF pulses. The response of the spin system is stretched over longer time allowing a more precise capture of the spin system evolution and, thus more precise determination of the relaxation times.

Electron Spin Echo imaging

Figure 9:
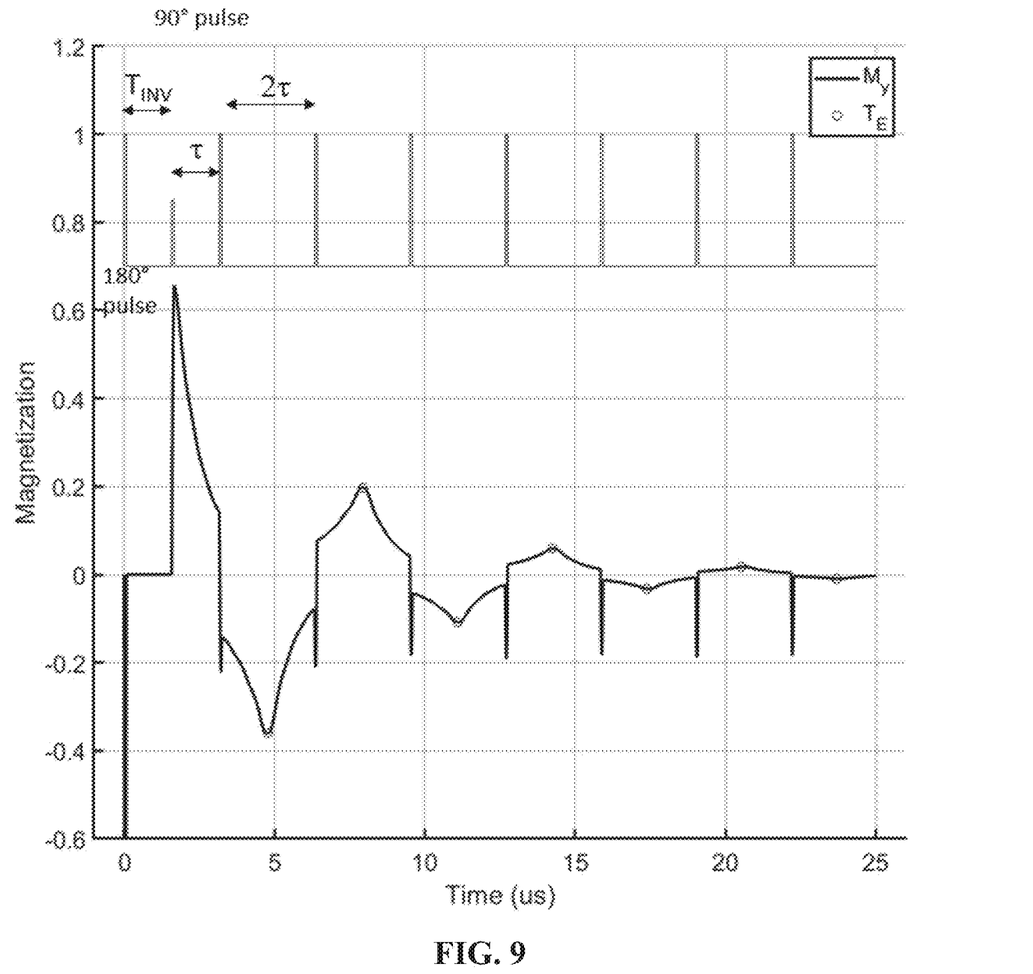
FIG. 9 illustrates magnetization amplitude as a function of time, according to an example of the present subject matter.

One implementation of a pulse train for electron spin echo imaging includes an inversion 180-degree pulse followed after delay $T_{INV}$ by CPMG pulse sequence used for $T_2$ mapping including a 90-degree pulse followed after delay $\tau$ by 180-degree pulse, followed after delay $2\tau$ by the train of 180-degree pulses separated by $2\tau$ delays (FIG. 9). All echo signals are detected and used for image reconstruction. Two images can be reconstructed separately from the rising and falling parts of the echo signals. The fourth dimension of the four-dimensional image will have a size equal to twice the number of detected echo shapes. The strength of the magnetic field gradient should be chosen so that the observable part of the echo shape can be mapped to k-space without omission of any k-space area.

FIG. 9 shows the response of spin system to the CPMG sequence of RF pulses computed using Bloch equations. The signals used for ESE image reconstruction are marked with open circles.

Various Notes

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method comprising:
    delivering a sequence of radio frequency (RF) pulses to a specimen having an electron paramagnetic resonance spin system, the pulses separated by equal time intervals and the sequence having a duration equal or greater than a spin-lattice relaxation time for the electron paramagnetic resonance spin system;
    receiving a response after each RF pulse in the sequence, the response including a free induction decay or a spin echo;
    generating a series of single point imaging (SPI) images, wherein each SPI image is in one-to-one relation with the response; and
    wherein an amplitude of the sequence of RF pulses is raised from zero to 90-degrees.

2. The method of claim 1 wherein the time intervals are shorter than an equilibration time between RF pulses and the spin system.

3. The method of claim 1 further including phase cycling for separation of free induction decays and spin echo responses.

4. The method of claim 1 further including generating a spatial quantitative map of at least one of: spin-spin $T_2$ relaxation time, $T_2^*$ relaxation time, spin-lattice $T_1$ relaxation time, and magnetic field $B_1$ by comparing the series of SPI images and a library of signal evolutions.

5. The method of claim 1 further including generating a $T_1$ and $T_2$ relaxation time map using a Bloch equation or using stored data.

6. The method of claim 1 further including generating a $B_1$ map using a Bloch equation or using stored data.

7. A method comprising:
    providing a pulse sequence to a spin system, the pulse sequence including a plurality of radio frequency pulses separated by time intervals, wherein the pulse sequence includes two pulses of differing amplitudes and includes two pulses of differing phase, wherein the pulse sequence has a duration greater than a $T_1$ relaxation time; and
    acquiring electron paramagnetic resonance (EPR) signals including free induction decays and spin echoes.

8. The method of claim 7 wherein providing the pulse sequence includes providing pulses at a fixed time interval.

9. The method of claim 7 wherein providing the pulse sequence includes providing pulses in which pulse amplitudes are raised from zero to 90-degrees.

10. The method of claim 7 further including separating free induction decays and echo signals from spurious signals in the acquired EPR signals.

11. The method of claim 7 further including comparing the acquired EPR signals with simulated signals based on a Bloch equation or based on stored data.

* * * * *